(12) United States Patent
Otsuka et al.

(10) Patent No.: US 7,741,085 B2
(45) Date of Patent: Jun. 22, 2010

(54) COMPOUND WS727713

(75) Inventors: Takanao Otsuka, Okayama (JP); Hirotsugu Ueda, Tokyo (JP); Keiko Fujie, Tokyo (JP); Hideyuki Muramatsu, Tokyo (JP); Michizane Hashimoto, Tokyo (JP); Shigehiro Takase, Tokyo (JP)

(73) Assignee: Astellas Pharma Inc., Chuo-Ku, Tokyo (JP)

( * ) Notice: Subject to any disclaimer, the term of this patent is extended or adjusted under 35 U.S.C. 154(b) by 733 days.

(21) Appl. No.: 11/547,729

(22) PCT Filed: Mar. 22, 2005

(86) PCT No.: PCT/JP2005/005653
§ 371 (c)(1),
(2), (4) Date: Oct. 6, 2006

(87) PCT Pub. No.: WO2005/097973
PCT Pub. Date: Oct. 20, 2005

(65) Prior Publication Data
US 2007/0254829 A1    Nov. 1, 2007

(30) Foreign Application Priority Data
Apr. 8, 2004  (AU) ............................. 2004901919

(51) Int. Cl.
*C12P 1/04* (2006.01)
*A61K 38/12* (2006.01)

(52) U.S. Cl. .................... 435/170; 435/252.1; 435/119; 514/10; 530/317; 530/321

(58) Field of Classification Search ................. 435/170, 435/119, 252, 1; 514/9, 10; 530/317, 321
See application file for complete search history.

(56) References Cited

U.S. PATENT DOCUMENTS 3,853,836 A    12/1974    Greven
6,074,872 A *   6/2000    Sutcliffe et al. ............. 435/325
6,133,003 A    10/2000    Rabenhorst et al.

FOREIGN PATENT DOCUMENTS

WO    WO 01/55106 A2    8/2001

OTHER PUBLICATIONS

Masutani et al. Proceedings of the Japan Academy, Series B: Physical and Biolgoical Sciences (2002) 78B(1): 15-17.*
S. D. Lee et al., Phylogenetic Analysis of the general Pseudonocardia and Actinobispora Based on 16S Ribosomal DNA Sequences; FEMS Microbiology Letters 182 (2000) pp. 125-129.

* cited by examiner

*Primary Examiner*—Sandra Saucier
*Assistant Examiner*—Susan Hanley
(74) *Attorney, Agent, or Firm*—Finnegan, Henderson, Farabow, Garrett & Dunner, L.L.P.

(57) ABSTRACT

The present invention relates to a compound WS727713, useful as a modulator of melanocortin receptors, and a process for its production by culturing in a culture medium the *actinomycetes* strain of the genus *Pseudonocardia*, deposit number FERM BP-7570 and recovering the compound.

3 Claims, 3 Drawing Sheets

SEQUENCE LISTING

<160> NUMBER OF SEQ ID NOS: 1

<210> SEQ ID NO 1
<211> LENGTH: 1483
<212> TYPE: DNA
<213> ORGANISM: Pseudonocardia sp. No.727713
<220> FEATURE:
<221> NAME/KEY: misc_feature
<222> LOCATION: (469)..(470)
<223> OTHER INFORMATION: n is a, c, g, or t
<220> FEATURE:
<221> NAME/KEY: misc_feature
<222> LOCATION: (530)..(530)
<223> OTHER INFORMATION: n is a, c, g, or t
<220> FEATURE:
<221> NAME/KEY: misc_feature
<222> LOCATION: (836)..(836)
<223> OTHER INFORMATION: n is a, c, g, or t
<220> FEATURE:
<221> NAME/KEY: misc_feature
<222> LOCATION: (865)..(865)
<223> OTHER INFORMATION: n is a, c, g, or t

<400> SEQUENCE: 1

```
gcacgaacgc tggcggcgtg cttaacacat gcaagtcgag cggtaaggcc tttcggggta    60
cacgagcggc gaacgggtga gtaacacgtg ggtgacctgc cctcagctct gggataagcc   120
tgggaaactg ggtctaatac cggatatgac ttcacatcgc atggtgtgtt gtggaaagtt   180
ttttcggctg gggatgggcc cgcggcctat cagcttgttg gtggggtgat ggcctaccaa   240
ggcgacgacg ggtagccggc ctgagagggc gaccggccac actgggactg agacacggcc   300
cagactccta cgggaggcag cagtggggaa tattgcgcaa tgggcggaag cctgacgcag   360
cgacgccgcg tggggatga cggccttcgg gttgtaaacc tctttcgcca gggacgaaga   420
gtgattgacg gtacctggat aagaagcacc ggccaactac gtgccagcnn ccgcggtaat   480
acgtagggtg cgagcgttgt ccggaattat tgggcgtaaa gagctcgtan gcggtgtgtc   540
gcgtcgatcg tgaaaacttg gggcttaact ctgagcttgc ggtcgatacg ggcatcactt   600
gagttcggca ggggagactg gaattcctgg tgtagcggtg aaatgcgcag atatcaggag   660
gaacaccggt ggcgaaggcg ggtctctggg ccgatactga cgctgaggag cgaaagcgtg   720
gggagcgaac aggattagat accctggtag tccacgccgt aaacggtggg cgctaggtgt   780
gggggccatt ccacggtctc tgtgccgcag caacgcatta agcgcccgc ctgggnagta   840
cggccgcaag gctaaaactc aaagnaattg acggggccc gcacaagcgg cggagcatgt   900
ggattaattc gatgcaacgc gaagaacctt acctggggttt gacatgcact agacgcacat   960
agagatatgt gttcccttgt ggctggtgtg caggtggtgc atggctgtcg tcagctcgtg  1020
tcgtgagatg ttgggttaag tcccgcaacg agcgcaaccc tcgttccatg ttgccagcgg  1080
gttatgccgg ggactcatgg gagactgccg ggtcaactc ggaggaaggt ggggatgacg  1140
tcaagtcatc atgccccttta tgtccagggc ttcacacatg ctacaatggc cagtacagag  1200
ggctgcgaga ccgtgaggtg gagcgaatcc cttaaagctg gtctcagttc ggattggggt  1260
ctgcaactcg accccatgaa gttggagtcg ctagtaatcg cagatcagca acgctgcggt  1320
gaatacgttc ccgggccttg tacacaccgc ccgtcacgtc acgaaagttg gtaacacccg  1380
aagccgacgg cctaacccgc ttgcgggagg gagtcgtcga aggtgggact ggcgattggg  1440
acgaagtcgt aacaaggtag ccgtaccgga aggtgcggct gta                    1483
```

COMPOUND WS727713

This application is a 371 of PCT/JP2005/005653, filed Mar. 22, 2005, which claims priority to Australian application No. 2004901919, filed Apr. 8, 2004.

TECHNICAL FIELD

The present invention relates to a new compound which is useful as a medicament or a cosmetic, to a process for producing the same and to a pharmaceutical composition comprising the same.

BACKGROUND ART

The melanocortin (MC) is a group of peptide hormones that are derived from posttranslational modifications by enzymatic cleavage of the preprohormone. The MCs include melanocyte-stimulating hormones (MSH) such as α-MSH, β-MSH and γ-MSH, as well as adenocorticotropic hormone (ACTH). These MCs regulate diverse physiological functions through membrane MC receptors (MC-Rs). Five MC-Rs (MC1-R, MC2-R, MC3-R, MC4-R and MC5-R) have been cloned and characterized. The MC1-R (the first discovered as α-MSH receptor) is expressed in integumental melanocytes and involved in epidermal melanin pigmentation and animal coloration.

Recently, it has been discovered that MC1-R is involved in pain and inflammation, and MC1-R mRNA is expressed in inflammatory cells such as neutrophils or mononuclear cells. It is likely that MC1-R account for the inhibitory actions of α-MSH on production of nitric oxide in monocytes and migration of neutrophils. Evidence has shown that the α-MSH molecules reduced inflammatory reaction in animal models of inflammatory responses in humans. α-MSH reduced inflammation which was induced in mouse skin by general irritants. Also, α-MSH inhibited mouse paw edema induced by carrageenan. Thus, MC1-R agonists are expected to be useful as a medicament against inflammatory reaction.

DISCLOSURE OF THE INVENTION

The present invention relates to a novel compound which is useful as a modulator of melanocortin receptors, to a process for producing the same and to a pharmaceutical or a cosmetic composition comprising the same.

More particularly, it relates to a melanocortin receptor agonist compound which has a reduction effect on inflammatory reaction.

The inventors of this invention also found that a melanocortin receptor modulator, such as the WS727713, has a potent anti-inflammatory effect. Therefore, a melanocortin receptor modulator, such as the WS727713, is useful as an active ingredient of an anti-inflammatory agent and useful as a therapeutical or prophylactic agent for diseases responsive to regulation of melanocortin receptors such as ischemia/reperfusion injury, brain inflammatory diseases, renal inflammatory diseases, hepatitis, sepsis/septic shock, hypoxic shock, acute respiratory distress syndrome (ARDS), rheumatic arthritis (RA), gouty arthritis, aortic regurgitation (AR), juvenile chronic arthritis, osteoarthritis, nephritis, induction of tolerance, contact hypersensitivity, inflammatory bowel disease (IBD), sexual dysfunction, transplantation, pain, disease progression of HIV, postinflammatory hypopigmentation, tinea versicolor, idiopathic guttate hypomelanosis, fever, functional bowel disease, obesity, satiety effect, diabetes mellitus, modulation of dermal exocrine function, canities (canities circumscripta), gray hair, pancreatitis, fibrotic disorders (hypertrophic scars, keloids, localized scleroderma, systematic sclerosis, sclerodermic graft versus host disease of the skin, cirrhosis of the liver, idiopathic and bleomycin induced lung fibrosis, cyclosporin induced nephropathy), uveitis (especially in Behçet's syndrome and sarcoidosis), vasculitis, microbial infections, celiac disease, vulvar vestibulitis syndrome, melanoma invasion, anorexia or the like.

Accordingly, one object of this invention is to provide a compound which has biological activities as stated above.

Another object of this invention is to provide a process for the production of WS727713 by fermentation of a WS727713-producing strain belonging to the genus *Pseudonocardia* in a culture medium.

A further object of this invention is to provide a pharmaceutical composition containing, as an active ingredient, the WS727713.

A yet further object of this invention is to provide a use of the melanocortin receptor modulators, such as WS727713, for treating and preventing diseases stated above.

Thus, the present invention provides the following.

(1) A substantially pure WS727713 compound having the following properties:
 a) Molecular formula: $C_{30}H_{44}N_8O_8$
 b) $^1$H Nuclear magnetic resonance spectrum: (500 MHz, DMSO-d6) δ 9.76 (1H, s, exchangeable), 8.76 (1H, d, J=7.5 Hz, exchangeable), 8.23 (1H, d, J=5 Hz, exchangeable), 7.76 (1H, dd, J=8.5 and 3 Hz, exchangeable); 7.25-7.17 (5H, m), 5.71 (1H, dd, J=10.5 and 5 Hz), 5.08 (1H, dd, J=11 and 4 Hz, exchangeable), 5.03 (1H, m), 4.99 (1H, m), 4.92 (1H, m), 4.85 (1H, m), 4.83 (1H, d, J=3 Hz, exchangeable), 4.76 (1H, br d, J=12 Hz, exchangeable), 4.12 (1H, dd, J=16.5 and 8.5 Hz), 3.65 (1H, dd, J=16.5 and 3 Hz), 3.58 (1H, m), 3.07 (1H, dd, J=13.5 and 8.5 Hz), 2.94 (1H, br d, J=13 Hz), 2.86 (1H, dd, J=13.5 and 6 Hz), 2.73-2.68 (2H, m), 2.58 (1H, m), 2.24 (1H, br d, J=13 Hz), 2.08 (1H, br d, J=14 Hz), 1.88 (1H, m), 1.67 (1H, m), 1.55 (1H, m), 1.42-1.36 (2H, m), 1.21 (1H, m), 1.19 (3H, d, J=7 Hz), 1.09 (1H, m), 0.76 (3H, d, J=6.5 Hz), 0.75 (3H, d, J=6.5 Hz).
 c) $^{13}$C Nuclear magnetic resonance spectrum: (125 MHz, DMSO-d6) δ 173.8 (s), 171.7 (s), 170.4 (s), 169.8 (s), 169.1 (s), 167.6 (s), 137.2 (s), 129.2 (d) x2, 128.0 (d) x2, 126.3 (d), 60.2 (d), 53.2 (t), 51.1 (d), 50.8 (d), 49.6 (d), 47.4 (d), 47.0 (t), 44.7 (d), 41.2 (t), 36.4 (t), 35.4 (t), 33.2 (t), 23.6 (d), 23.5 (t), 23.1 (q), 21.7 (q), 21.0 (t), 15.8 (q).

(2) An *actinomycetes* strain belonging to the genus *Pseudonocardia*, which has a deposit number FERM BP-7570.

(3) A compound having a melanocortin receptor modulatory activity, which is obtained by culturing the *actinomycetes* strain of (2) above in a culture medium and recovering the compound from a culture broth thereof.

(4) A process for producing the WS727713 compound of (1) above, which comprises culturing, in a culture medium, a WS727713-producing strain belonging to the genus *Pseudonocardia* and recovering the compound from a culture broth thereof.

(5) The process of (4) above, wherein the WS727713-producing strain belonging to the genus *Pseudonocardia* is the *actinomycetes* strain of (2) above.

(6) A pharmaceutical or a cosmetic composition containing the WS727713 compound of (1) above or a salt thereof and a pharmaceutically acceptable, substantially non-toxic carrier or excipient.

(7) A compound of (1) above for use as a medicament or a cosmetic.

(8) A process for producing a compound having a melanocortin receptor modulatory activity, which comprises culturing, in a culture medium, an *actinomycetes* strain belonging to the genus *Pseudonocardia*, which produces a compound having a melanocortin receptor modulatory activity, and recovering said compound.

(9) A compound having a melanocortin receptor modulatory activity, which is obtained by culturing, in a culture medium, an *actinomycetes* strain belonging to the genus *Pseudonocardia*, which produces a compound having melanocortin receptor modulatory activity, and recovering the compound from a culture broth thereof.

(10) A melanocortin receptor modulator comprising a compound of (1) above or a salt thereof.

(11) A method for modulating melanocortin receptor, comprising administering a compound of (1) abode or a salt thereof to a human being or an animal.

(12) Use of a compound of (1) above or a salt thereof for the manufacture of a medicament or a cosmetic for modulating melanocortin receptor.

(13) A pharmaceutical or a cosmetic composition for treating or preventing ishemia/reperfusion injury, brain and renal inflammatory diseases, hepatitis, sepsis/septic shock, hypoxic shock, acute respiratory distress syndrome (ARDS), rheumatic arthritis (RA), gouty arthritis, aortic regurgitation (AR), juvenile chronic arthritis, osteoarthritis, nephritis, induction of tolerance, contact hypersensitivity, inflammatory bowel disease (IBD), sexual dysfunction, transplantation, pain, disease progression of HIV, postinflammatory hypopigmentation, tinea versicolor, idiopathic guttate hypomelanosis, fever, functional bowel disease, obesity, satiety effect, diabetes mellitus, modulation of dermal exocrine function, canities (canities circumscripta), gray hair, pancreatitis fibrotic disorders (hypertrophic scars, keloids, localized scleroderma, systematic sclerosis, sclerodermic graft versus host disease of the skin, cirrhosis of the liver, idiopathic and bleomycin induced lung fibrosis, cyclosporin induced nephropathy), uveitis (especially in Behçet's syndrome and sarcoidosis), vasculitis, microbial infections, celiac disease, vulvar vestibulitis syndrome, melanoma invasion or anorexia, which comprises a compound of (1) above or a salt thereof and a pharmaceutically acceptable, substantially non-toxic carrier or excipient.

(14) A method for treating or preventing ishemia/reperfusion injury, brain and renal inflammatory diseases, hepatitis, sepsis/septic shock, hypoxic shock, acute respiratory distress syndrome (ARDS), rheumatic arthritis (RA), gouty arthritis, aortic regurgitation (AR), juvenile chronic arthritis, osteoarthritis, nephritis, induction of tolerance, contact hypersensitivity, inflammatory bowel disease (IBD), sexual dysfunction, transplantation, pain, disease progression of HIV, postinflammatory hypopigmentation, tinea versicolor, idiopathic guttate hypomelanosis, fever, functional bowel disease, obesity, satiety effect, diabetes mellitus, modulation of dermal exocrine function, canities (canities circumscripta), gray hair, pancreatitis, fibrotic disorders (hypertrophic scars, keloids, localized scleroderma, systematic sclerosis, sclerodermic graft versus host disease of the skin, cirrhosis of the liver, idiopathic and bleomycin induced lung fibrosis, cyclosporin induced nephropathy), uveitis (especially in Behçet's syndrome and sarcoidosis), vasculitis, microbial infections, celiac disease, vulvar vestibulitis syndrome, melanoma invasion or anorexia, which comprises administering a compound of (1) above or a salt thereof to a human being or an animal.

(15) Use of a compound of (1) above or a salt thereof for the manufacture of a medicament for treating or preventing ishemia/reperfusion injury, brain and renal inflammatory diseases, hepatitis, sepsis/septic shock, hypoxic shock, acute respiratory distress syndrome (ARDS), rheumatic arthritis (RA), gouty arthritis, aortic regurgitation (AR), juvenile chronic arthritis, osteoarthritis, nephritis, induction of tolerance, contact hypersensitivity, inflammatory bowel disease (IBD), sexual dysfunction, transplantation, pain, disease progression of HIV, postinflammatory hypopigmentation, tinea versicolor, idiopathic guttate hypomelanosis, fever, functional bowel disease, obesity, satiety effect, diabetes mellitus, modulation of dermal exocrine function, canities (canities circumscripta), gray hair, pancreatitis, fibrotic disorders (hypertrophic scars, keloids, localized scleroderma, systematic sclerosis, sclerodermic graft versus host disease of the skin, cirrhosis of the liver, idiopathic and bleomycin induced lung fibrosis, cyclosporin induced nephropathy), uveitis (especially in Behçet's syndrome and sarcoidosis), vasculitis, microbial infections, celiac disease, vulvar vestibulitis syndrome, melanoma invasion or anorexia.

BEST MODE FOR CARRYING OUT THE INVENTION

Figure 1:
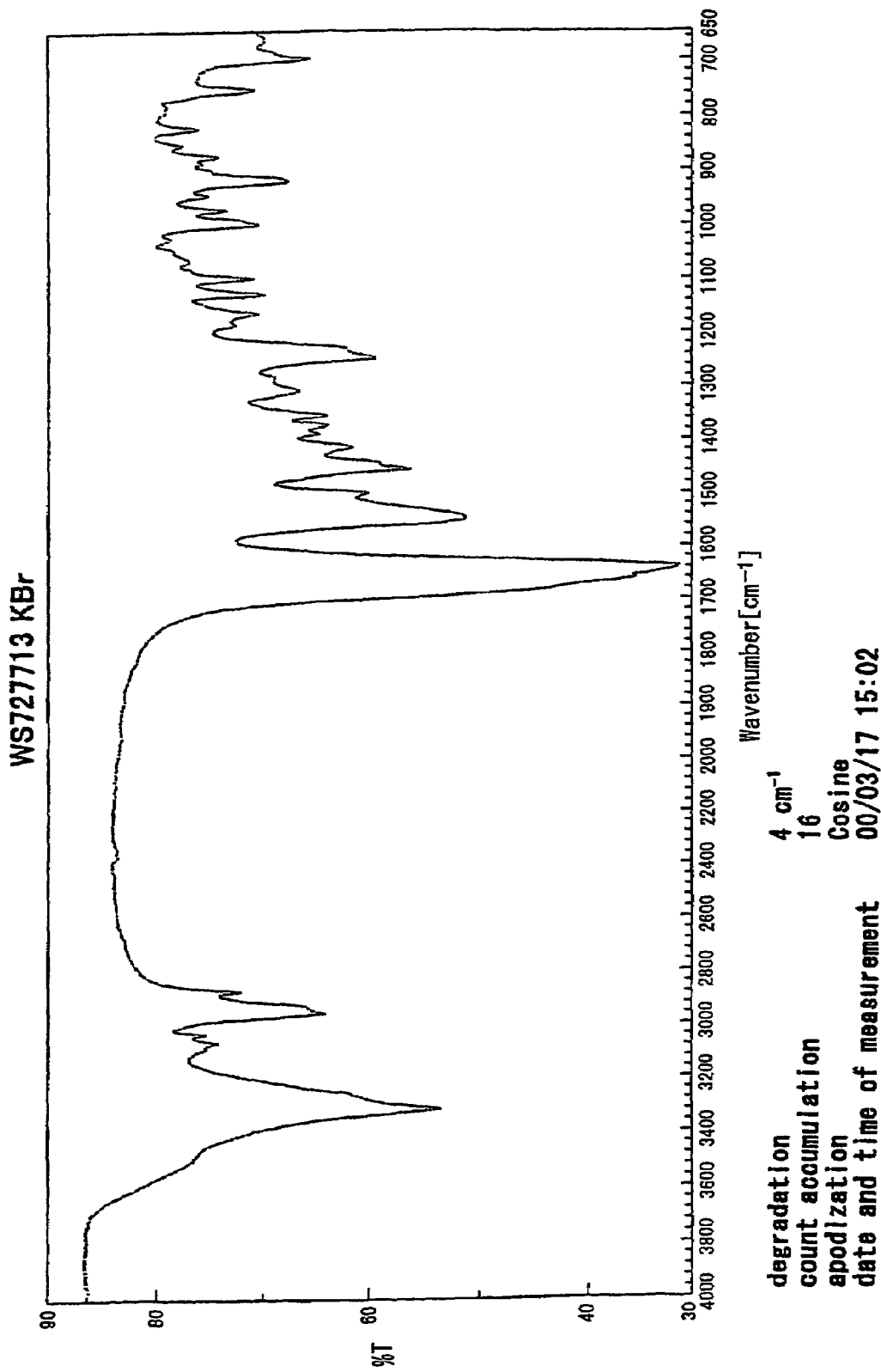
FIG. 1 shows a chart of infrared spectrum.
Figure 2:
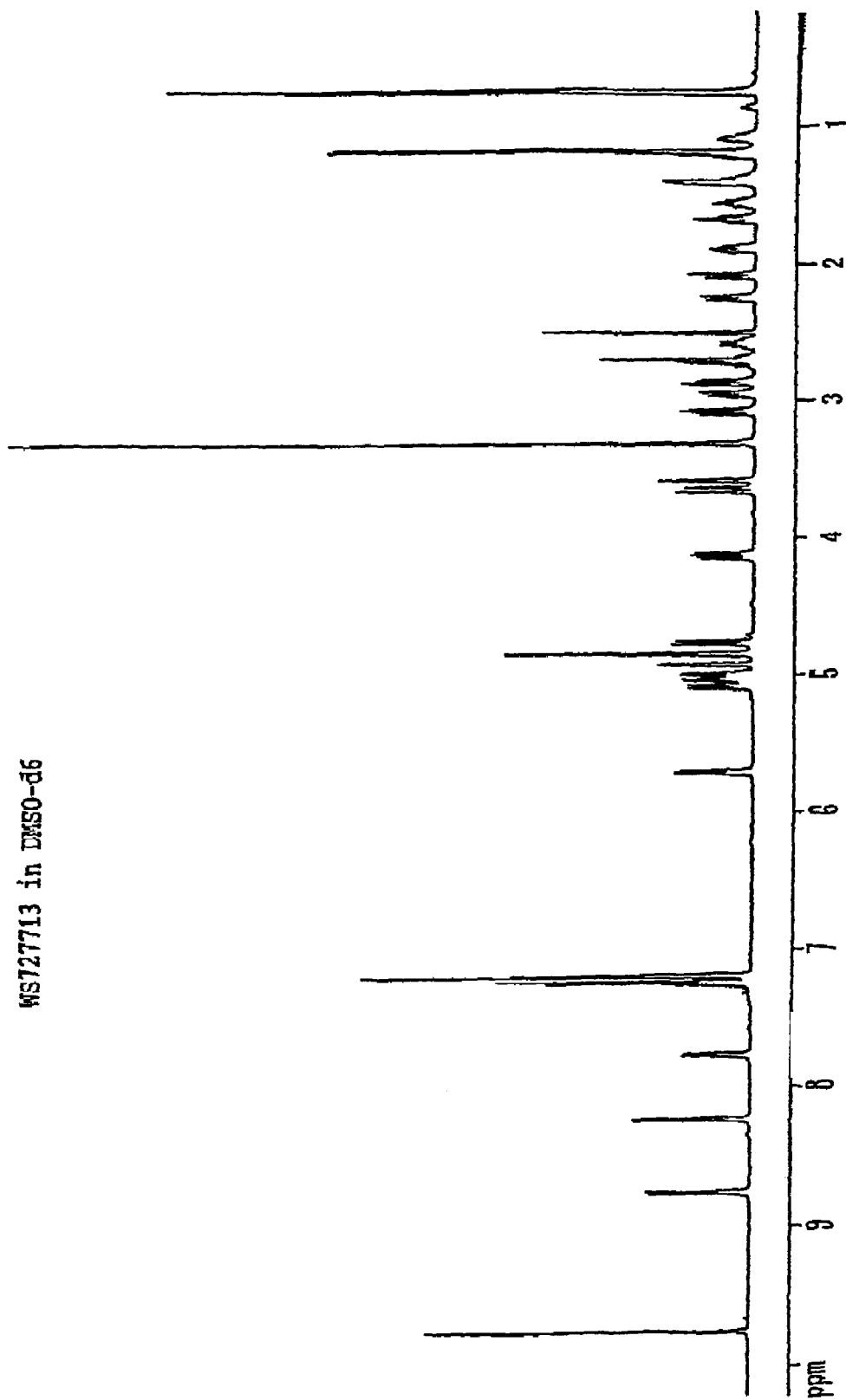
FIG. 2 shows a chart of $^1$H nuclear magnetic resonance spectrum.
Figure 3:
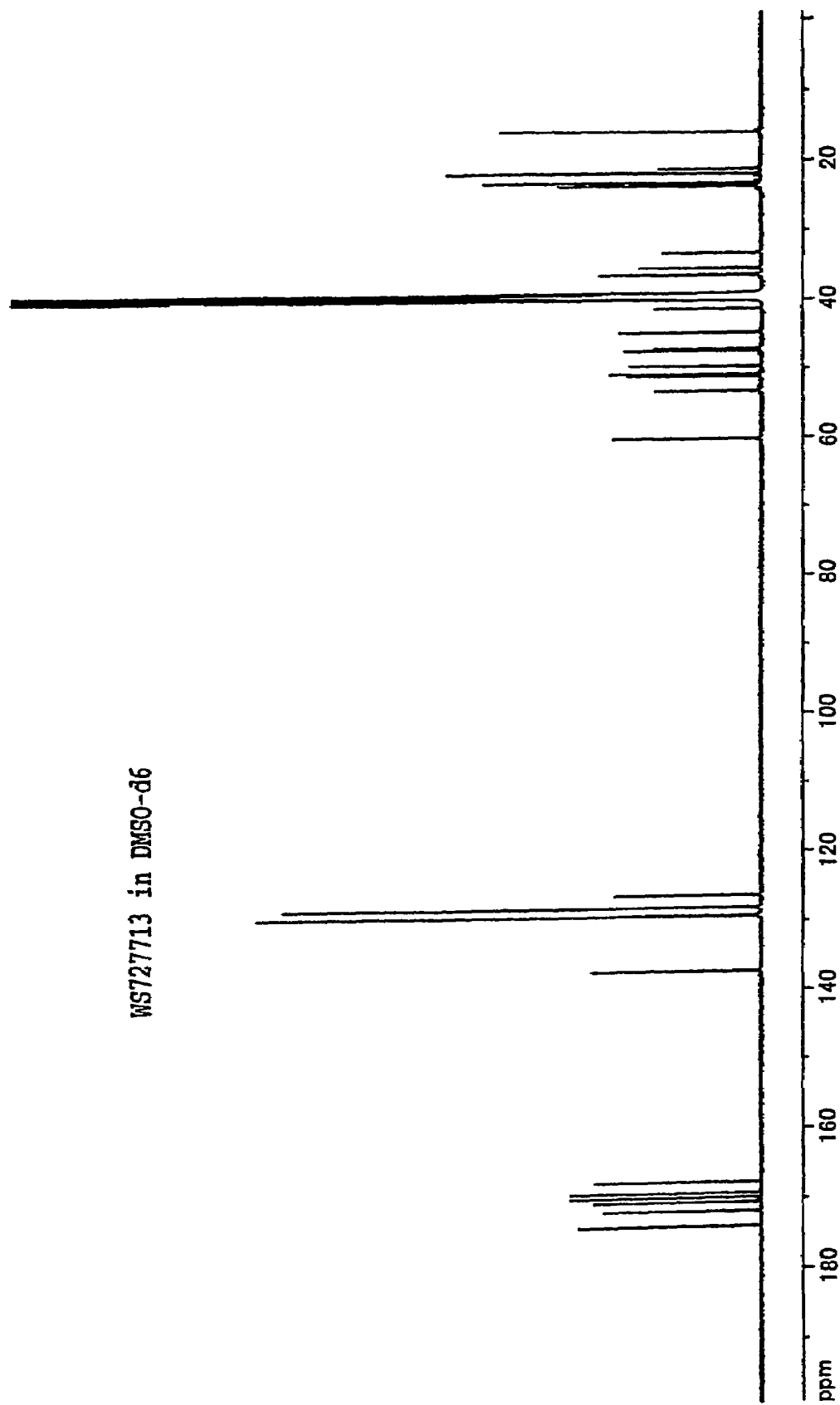
FIG. 3 shows a chart of $^{13}$C nuclear magnetic resonance spectrum.

The compound, which has a potent modulation effect on the activity of melanocortin receptor, can be characterized by the following properties. The charts of Infrared spectrum, $^1$H Nuclear magnetic resonance spectrum and $^{13}$C Nuclear magnetic resonance spectrum are shown in FIGS. 1-3.

a) Molecular formula: $C_{30}H_{44}N_8O_8$
b) ESI-MS (+:m/z): 645(M+H)$^+$
c) Infrared spectrum (FIG. 1):
vmax (KBr): 3310, 2950, 1640, 1545, 1450, 1410, 1370, 1350, 1300, 1245, 1160, 1125, 1095, 995 cm$^{-1}$
d) $^1$H Nuclear magnetic resonance spectrum (FIG. 2): (500 MHz, DMSO-d6) δ 9.76 (1H, s, exchangeable), 8.76 (1H, d, J=-7.5 Hz, exchangeable), 8.23 (1H, d, J=5 Hz, exchangeable), 7.76 (1H, dd, J=8.5 and 3 Hz, exchangeable), 7.25-7.17 (5H, m), 5.71 (1H, dd, J=10.5 and 5 Hz), 5.08 (1H, dd, J=11 and 4 Hz, exchangeable), 5.03 (1H, m), 4.99 (1H, m), 4.92 (1H, m), 4.85 (1H, m), 4.83 (1H, d, J=3 Hz, exchangeable), 4.76 (1H, br d, J=12 Hz, exchangeable), 4.12 (1H, dd, J=16.5 and 8.5 Hz), 3.65 (1H, dd, J=16.5 and 3 Hz), 3.58 (1H, m), 3.07 (1H, dd, J=13.5 and 8.5 Hz), 2.94 (1H, br d, J=13 Hz), 2.86 (1H, dd, J=13.5 and 6 Hz), 2.73-2.68 (2H, m), 2.58 (1H, m), 2.24 (1H, br d, J=13 Hz), 2.08 (1H, br d, J=14 Hz), 1.88 (1H, m), 1.67 (1H, m), 1.55 (1H, m), 1.42-1.36 (2H, m), 1.21 (1H, m), 1.19 (3H, d, J=7 Hz), 1.09 (1H, m), 0.76 (3H, d, J=6.5 Hz), 0.75 (3H, d, J=6.5 Hz).
e) $^{13}$C Nuclear magnetic resonance spectrum (FIG. 3): (125 MHz, DMSO-d6) δ 173.8 (s), 171.7 (s), 170.4 (s), 169.8 (s), 169.1 (s), 167.6 (s), 137.2 (s), 129.2 (d) x2, 128.0 (d) x2, 126.3 (d), 60.2 (d), 53.2 (t), 51.1 (d), 50.8 (d), 49.6 (d), 47.4 (d), 47.0 (t), 44.7 (d), 41.2 (t), 36.4 (t), 35.4 (t), 33.2 (t), 23.6 (d), 23.5 (t), 23.1 (q), 21.7 (q), 21.0 (t), 15.8 (q).

In particular, the WS727713 has the following physicochemical properties:
Molecular formula:

$C_{30}H_{44}N_8O_8$

ESI-MS (+:m/z): 645 (M+H)$^+$
HR-ESI-TOF/MS (+:m/z)

| calculated | 645.3360(M + H)+ |
| found | 645.3387(M + H)+ |

Specific rotation: $[\alpha]_D(23°\text{ C.})\ 32°\ (c=0.5,\ \text{in DMSO})$

Solubility: Soluble: methanol, acetonitrile, acetone, ethyl acetate, DMSO Poorly soluble: $H_2O$ Color reaction Positive: iodine vapor reaction, cerium sulfate reaction, Ehrlich reaction, Dragendorff reaction Negative: Molish reaction, ninhydrin reaction Thin layer chromatography (TLC):

| Stationary phase | Developing solvent | Rf value |
|---|---|---|
| Silica Gel 60 F254* | $CHCl_3:CH_3OH = 10:1$ | 0.45 |
| RP-18W F254S HPTLC* | MeCN:water = 80:20 | 0.53 |

*made by E. Merck

High performance liquid chromatography (HPLC):

Conditions: Mobile phase: 35% aqueous acetonitrile Column: Mightysil RP-18 GP (4.6×150 mm) Flow rate: 1.0 ml/minute Detection: UV at 210 nm Retention time: 9.3 minutes Infrared spectrum (FIG. 1): vmax (KBr): 3310, 2950, 1640, 1545, 1450, 1410, 1370, 1350, 1300, 1245, 1160, 1125, 1095, 995 $cm^{-1}$ $^1H$ Nuclear magnetic resonance spectrum (FIG. 2): (500 MHz, DMSO-d6) δ 9.76 (1H, s, exchangeable), 8.76 (1H, d, J=7.5 Hz, exchangeable), 8.23 (1H, d, J=5 Hz, exchangeable), 7.76 (1H, dd, J=8.5 and 3 Hz, exchangeable), 7.25-7.17 (5H, m), 5.71 (1H, dd, J=10.5 and 5 Hz), 5.08 (1H, dd, J=11 and 4 Hz, exchangeable), 5.03 (1H, m), 4.99 (1H, m), 4.92 (1H, m), 4.85 (1H, m), 4.83 (1H, d, J=3 Hz, exchangeable), 4.76 (1H, br d, J=12 Hz, exchangeable), 4.12 (1H, dd, J=16.5 and 8.5 Hz), 3.65 (1H, dd, J=16.5 and 3 Hz), 3.58 (1H, m), 3.07 (1H, dd, J=13.5 and 8.5 Hz), 2.94 (1H, br d, J=13 Hz), 2.86 (1H, dd, J=13.5 and 6 Hz), 2.73-2.68 (2H, m), 2.58 (1H, m), 2.24 (1H, br d, J=13 Hz), 2.08 (1H, br d, J=14 Hz), 1.88 (1H, m), 1.67 (1H, m), 1.55 (1H, m), 1.42-1.36 (2H, m), 1.21 (1H, m), 1.19 (3H, d, J=7 Hz), 1.09 (1H, m), 0.76 (3H, d, J=6.5 Hz), 0.75 (3H, d, J=6.5 Hz).

$^{13}C$ Nuclear magnetic resonance spectrum (FIG. 3): (125 MHz, DMSO-d6) δ 173.8 (s), 171.7 (s), 170.4 (s), 169.8 (s), 169.1 (s), 167.6 (s), 137.2 (s), 129.2 (d) x2, 128.0 (d) x2, 126.3 (d), 60.2 (d), 53.2 (t), 51.1 (d), 50.8 (d), 49.6 (d), 47.4 (d), 47.0 (t), 44.7 (d), 41.2 (t), 36.4 (t), 35.4 (t), 33.2 (t), 23.6 (d), 23.5 (t), 23.1 (q), 21.7 (q), 21.0 (t), 15.8 (q).

Color and condition: White crystal

Melting point: 272-277° C. (decomposition)

Characteristics of the Producing Strain No.727713

Strain No. 727713 was isolated from a leaf litter sample collected at Chiba Prefecture, Japan. For the taxonomic study of strain No. 727713, the methods and media described by Shirling and Gottlieb (Shirling, E. B. and D. Gottlieb: Methods for characterization of *Streptomyces* species. Int. J. Syst. Bacteriol. 16, 313-340, 1966), and by Waksman (Waksman, S. A.: The *actinomycetes* Vol. 2: Classification, identification and description of genera and species: The Williams and Wilkins Co., Baltimore, 1961) were employed. The observations were made after cultivating for 14 days at 30° C. The morphological observations were made on the cultures grown on humic acid-vitamin agar (Hayakawa, M. and Nonomura, H.: Humic acid-vitamin agar, a new medium for the selective isolation of soil *actinomycetes*. J. Ferment. Technol., 65, 501-509, 1987), using an optical microscope and a scanning electron microscope. The range of temperature for growing was determined on yeast extract-starch agar containing 2 g of yeast extract (Daigo Eiyo, Osaka, Japan), 10 g of soluble starch, and 16 g of agar in 1000 ml of tap water (adjusted to pH 7.2 with 1N NaOH before sterilized). Carbon utilization was determined on Pridoham and Gottlieb's medium (Pridoham, T. G. and D. Gottlieb: The utilization of carbon compounds by some Actinomycetales as an acid for species determination: J. Bacteriol. 56: 107-114, 1948) added 0.1% yeast extract. The color names used in this study were taken from Methuen Handbook of Colour (Kornerup, A. and J. H. Wanscher: Methuen Handbook of Colour, Methuen, London, 1978). The preparation of cells and the detection of the isomer of diaminopimeric acid were performed by the procedure of Becker et al. (Becker, B., M. P. Lechevalier, R. E. Gordon and H. A. Lechevalier: Rapid differentiation between *Nocardia* and *Streptomyces* by paper chromatography of whole-cell hydrolysates: Appl. Microbiol. 12, 421-423, 1964). The whole-cell sugar composition was determined by the method of Lechevalier and Lechevalier (Lechevalier, M. P. and H. A. Lechevalier: Chemical composition as a criterion in the classification of aerobic *actinomycetes*. Int. J. Syst. Bacteriol., 20, 435-443, 1970). The 16S rDNA sequence was determined by the method of Reichert et al. (Katrin Reichert, Andre Lipski, Silke Pradella, Erko Stackebrandt and Karlheinz Altendorf: *Pseudonocardia asaccharolytica* sp. nov. and *Pseudonocardia sulfidoxydans* sp. nov., two new dimethyl disulfide-degrading *actinomycetes* and emended description of the genus *Pseudonocardia*: Int. J. Syst. Bacteriol. 48, 441-449, 1998). The 16S rDNA sequences of type strains were obtained from DDBJ data base (http://www.ddbj.nig.ac.jp). The phylogenetic tree was constructed with CLUSTAL program (Thompson, J. D., Gibson, T. J., Plewniak, F., Jeanmougin, F. and Higgins, D. G.: The CLUSTAL X windows interface: flexible stradesies for multiple sequence alignment aided by quality analysis tools. Nucleic Acids Res. 24: 4876-4882, 1997).

Its bacteriological characteristics were as follows.

The cultural characteristics on various agar media and the physiological characteristics are shown in Table 1 and 2 respectively. The strain growth was observed on yeast extract-malt extract agar, oatmeal agar, and pepton-yeast extract-iron agar, but not on Inorganic salts-starch agar, Glycerol-asparagine agar, and Tyrosine agar. Aerial mycerium was observed only on humic acid-vitamin agar, and its aerial mass color was white. Reverse side color of growth was light orange. Melanoid pigments were not produced in trypton-yeast extract broth and peptone-yeast extract-iron agar. Soluble pigments were not produced. Mycerial mass color was not pH sensitive.

As morphological characteristics, the substrate mycelium developed well and branched irregularly. Formation of swollen hyphal segments was observed. This strain produced aerial mycelium with straight spore chains which comprised more than 10 spores per chain. Spores were spindle (1.6-2.3× 0.5-0.6 μm) in shape. The surfaces of them were smooth. Sclerotic granules, sporangia and motile spores or fragments were not observed.

Strain No.727713 was able to grow in the temperature range of from 11 to 32° C., with the growth optimum at 28° C.

Meso-Diaminopimelic acid, lactose, and arabinose were detected in the whole-cell hydrolysates of this strain, and cell wall type was type IV.

The partial sequence of strain No. 727713 is shown in SEQ ID NO:1 in the sequence listing. Similarity values of the 16S rDNA between strain No. 727713 and members of the genus

*Pseudonocardia* are 91.8-97.4%, and they make single cluster on the phylogenetic tree (Data not shown).

Based on the morphological and chemical characteristics and phylogenetic analysis described above, strain No.727713 is considered to belong to the genus *Pseudonocardia* (Lechevalier, M. P. and H. A. Lechevalier: Chemical composition as a criterion in the classification of aerobic *actinomycetes*. Int. J. Syst. Bacteriol., 20, 435-443, 1970; Pridham, T. G., et al.: Appl. Microbiol. 6: 54, 1958). Therefore, this strain was designated as *Pseudonocardia* sp. No. 727713. The strain has been deposited at the International Patent Organism Depositary, National Institute of Advanced Industrial Science and Technology, AIST Tsukuba Central 6, 1-1, Higashi 1-chome, Tsukuba-shi, Ibaraki-ken, 305-8566, Japan, as FERM BP-7570 (deposition date: Apr. 25, 2001).

TABLE 1

Cultural characteristics of strain No. 727713.

| Media | Cultural characteristics |
|---|---|
| Yeast extract-malt extract agar (ISP-2) | G: Good<br>A: Not observed<br>R: Light orange (5A5)<br>S: Not detected |
| Oatmeal agar (ISP-3) | G: Moderate<br>A: Not observed<br>R: Light orange (5A5)<br>S: Not detected |
| Inorganic salts-starch agar (ISP-4) | G: Not observed |
| Glycerol-asparagine agar (ISP-5) | G: Not observed |
| Peptone-yeast extract-iron agar (ISP-6) | G: Weak<br>A: Not observed<br>R: Light orange (5A5)<br>S: Not detected |
| Tyrosine agar | G: Not observed |

Abbreviation A: aerial mycerium, G: growth, S: soluble pigment, R: reverse color.

These characteristics were observed after 14 days of incubation at 30° C. The color descriptions are based on Methuen Handbook of Colour (Kornerup, A. and J. H. Wanscher, 3rd ed., pp. 252, Methuen, London, 1978).

TABLE 2

Physiological characteristics of strain No. 727713.

| Conditions | Characteristics |
|---|---|
| Temperature range for growth | 11-32° C. |
| Optimum temperature for growth | 28° C. |
| Production of melanoid pigments | − |
| Production of soluble pigments | − |
| Carbon utilization | |
| D-Glucose | + |
| Sucrose | + |
| D-Xylose | + |
| D-Fructose | + |
| L-Rhamnose | ± |
| Raffinose | + |
| L-Arabinose | + |
| Inositol | + |
| D-Mannitol | + |

It is to be understood that the production of the WS727713 is not limited to the use of the particular organism described herein, which is given for the illustrative purpose only. This invention also includes the use of any mutants which are capable of producing the WS727713 including natural mutants as well as artificial mutants which can be produced from the described organism by conventional means such as recombinant DNA technology, irradiation of X-ray, ultraviolet radiation, treatment with N-methyl-N'-nitro-N-nitrosoguanidine, 2-aminopurine, and the like.

Production of the WS727713

Of the compounds which has the above-mentioned properties, the WS727713 is produced when the WS727713-producing strain belonging to the *Pseudonocardia* is grown in a culture medium containing sources of assimilable carbon and nitrogen under aerobic conditions (e.g. shaking culture, submerged culture, etc.).

The preferred sources of carbon in the culture medium are carbohydrates such as glucose, sucrose, starch, fructose or glycerin, or the like.

The preferred sources of nitrogen are peanut powder, yeast extract, beef extract, peptone, polypeptone, gluten meal, cotton seed flour, soybean powder, soybean meal, corn steep liquor, dried yeast, wheat germ, etc., as well as inorganic and organic nitrogen compounds such as ammonium salts (e.g. ammonium nitrate, ammonium sulfate, ammonium phosphate, etc.), urea or amino acid, or the like.

The carbon and nitrogen sources, though advantageously employed in combination, need not be used in their pure form because less pure materials, which contain traces of growth factors and considerable quantities of mineral nutrients, are also suitable for use.

When desired, there may be added to the medium mineral salts such as sodium or calcium carbonate, sodium or potassium phosphate, sodium or potassium chloride, sodium or potassium iodide, magnesium salts, copper salts, zinc salts, iron salts, or cobalt salts, or the like.

If necessary, especially when the culture medium foams seriously, a defoaming agent, such as liquid paraffin, fatty oil, plant oil, mineral oil, silicone, or the like may be added.

Agitation and aeration of the culture mixture may be accomplished in a variety of ways, such as agitation by a propeller or similar mechanical agitation equipment, by revolving or shaking the fermentor, and the like.

The fermentation is usually conducted at a temperature between about 10° C. and 40° C., preferably 20° C. to 30° C., for a period of about 50 hours to 150 hours, which may be varied according to fermentation conditions and scales.

The resultant culture broth is then subjected for recovery of the WS727713 to various procedures conventionally used for recovery and purification of biological active substances, for instance, solvent extraction with an appropriate solvent or a mixture of some solvents, chromatography or recrystallization from an appropriate solvent or a mixture thereof.

WS727713 can be in the form of a solvate, which is within the scope of the present invention. The solvate preferably includes a hydrate and an ethanolate.

As examples for showing biological properties of the compounds of the above, some biological data are shown in the following.

Test 1. Binding Assay

Binding buffer was composed of 25 mM HEPES-KOH (pH 7.0), 1.5 mM $CaCl_2$, 1 mM $MgSO_4$, 100 mM NaCl, 1 mM 1,10-phenanthroline, 0.2% BSA, and 1 Complete TM Protease Inhibitor tablet/100 mL (Boehringer-Mannheim). Binding assay was modified by the method of Receptor Biology, Inc. Membrane suspension (25 µl), [$^{125}$I]-NDP-MSH (25 µl, NEN, $3.08 \times 10^{-11}$ M final), buffer (50 µl) and inhibitor were incubated for 60 min at 37° C. Then the mixture was filtered over GF/C (presoaked in 0.5% polyethyleneimine), and washed twice with ice cold PBS (−). The radioactivities trapped on a GF/C filter were measured using a Top Counter (Packard) after drying.

B16 cells were grown in RPMI1640 supplemented with 10% FBS and antibiotics. Sub-confluent cells were washed twice with ice-cold PBS (−) and scraped. The cells were then sonicated and centrifuged at 2,000 rpm at 4° C. for 5 min. Supernatant thus obtained was centrifuged at 30,000 rpm at 4° C. for 60 min. Membrane fraction was suspended with ice cold PBS (−) and stocked at −80° C.

Final concentrations of each receptor protein were as follows: MC1-R (B16), 0.139 mg/ml; MC3-R (recombinant*), 0.0693 mg/ml; MC4-R (recombinant*), 0.104 mg/ml; and MC5-R (recombinant*), 0.070 mg/ml (*: from Receptor Biology, Inc.)

As shown in Table 3, WS727713 inhibited the binding of [$^{125}$I]-NDP-MSH to melanocortin receptors. The result shows that WS727713 will work as an agonist or an antagonist for melanocortin receptors.

TABLE 3

Effects of WS727713 and NDP-MSH on the binding of [$^{125}$I]-NDP-MSH to melanocortin receptors

| IC50 (M) | MC1-R | MC3-R | MC4-R | MC5-R |
|---|---|---|---|---|
| NDP-MSH | $4.05 \times 10^{-11}$ | $8.15 \times 10^{-11}$ | $2.64 \times 10^{-10}$ | $5.58 \times 10^{-10}$ |
| WS727713 | $1.21 \times 10^{-7}$ | $4.16 \times 10^{-6}$ | $1.81 \times 10^{-6}$ | $2.50 \times 10^{-6}$ |

Test 2. A Dose-dependent Reduction of LPS-induced TNF-α Production in Mice by WS727713

Tumor necrosis factor (TNF-α) underlies pathological processes and functional disturbances in acute and chronic inflammatory disease and injury. The neuroimmunomodulatory peptide α-MSH modulates action and production of proinflammatory cytokines including TNF-α. To test for WS727713, male mice (ICR) were injected intraperitoneally with either lipopolysaccharide (LPS; Sigma, L-3129, E. coli 0127:B8, 100 μg/head) in saline or saline alone in two repeated experiments. WS727713 were injected intraperitoneally 30 min before LPS injection. Mice were sacrificed 60 min after LPS injection. Serum TNF-α levels were measured using enzyme-linked immunosorbent assay (TNF-α ELISA kit; Amersham). The result is shown in Table 4.

As shown in Table 4, the LPS-induced TNF-α level was reduced by the administration of WS727713 in a dose-dependent manner. The result shows that WS727713 has the function as a melanocortin receptor agonist.

TABLE 4

Effect of WS727713 on LPS-induced TNF-α production in mice

| | Serum TNF-α level (pg/ml) | Inhibition (%) |
|---|---|---|
| Vehicle Control (0.5% MC/saline) | 8533 ± 1602 | 0 |
| WS727713 (10 mg/kg i.p.) | 3695 ± 385 | 56.7 |
| WS727713 (32 mg/kg i.p.) | 2556 ± 892 | 70.0 |
| WS727713 (100 mg/kg i.p.) | 2038 ± 973 | 76.1 |
| NDP-MSH (100 μg/head i.p.) | 4808 ± 175 | 43.7 |
| NDP-MSH (100 μg/head i.v.) | 2187 ± 1120 | 74.4 |

MC: methylcellulose

The substantially pure compound of WS727713 is a modulator of the melanocortin receptors MC1-R, MC3-R, MC4-R and/or MC5-R, in particular having the agonist activity of MC1-R. The pharmaceutical composition comprising the substantially pure compound of WS727713 is useful as a therapeutic or prophylactic agent for diseases caused by inflammatory or immune condition. Further, it is useful to treat inflammation, particularly inflammation caused by the activation of the NF-κB and/or release of inflammatory cytokines.

Furthermore, pharmaceutical preparations comprising the substantially pure compound of the WS727713 are useful for the therapy and prophylaxis of the following diseases.

Diseases associated with chronic and acute inflammation and immune-modulation such as inflammatory bowel disease, irritable bowel syndrome, celiac disease, gall bladder disease, Chrohn's disease, ulcerative colitis, rheumatoid arthritis, gouty arthritis, osteoarthritis, osteoporosis, traumatic arthritis, rubella arthritis, muscle degeneration, pancreatitis (acute or chronic), psoriasis, glomerulonephritis, serum sickness, lupus (systematic lupus erythematosis), urticaria, scleraclerma, scleroderma, chronic thyroiditis, Grave's disease, dermatitis (contact or atopic), vulvar vestibulitis syndrome, dermatomyositis, alopecia, atopic eczemas, ichthyosis, fever, sepsis, migraine, cluster headaches, Alzheimer's disease, Parkinson's disease, Creutzfeldt-Jacob disease, multiple sclerosis, tuberculosis, dementia, and transplant or graft-host rejections (e.g., kidney, liver, heart, lung, pancreas, bone marrow, cornea, small bowel, skin allografts, skin homografts and heterografts, etc.).

Respiratory allergies and diseases such as asthma, acute respiratory distress syndrome, hayfever, allergic rhinitis, and chronic obstructive pulmonary disease; inflammatory disorders of the central nervous system such as HIV encephalitis, cerebral malaria, meningitis, and ataxia telangiectasis; and pain such as post-operative pain, neuromuscular pain, headache, pain caused by cancer, dental pain and arthritis pain.

Viral and autoimmune diseases such as herpes simplex type 1 (HSV-1), herpes simplex type 2 (HSV-2), cytomegalovirus, Epstein-Barr, human immunodeficiency virus (HIV), Addison's disease (autoimmune disease of the adrenal glands), idiopathic adrenal insufficiency, autoimmune polyglandular disease (also known as autoimmune polyglandular syndrome), chronic active hepatitis or acute hepatitis infection (including hepatitis A, hepatitis B, and hepatitis C), autoimmune gastritis, autoimmune hemolytic anemia, and autoimmune neutropenia; and fungal infections such as mycosis fungoides.

Diseases of the cardiovascular system such as atherosclerosis, transplant atherosclerosis, peripheral vascular disease, inflammatory vascular disease, intermittent claudication, restenosis, cerebrovascular stroke, transient ischemic attack, myocardial ischemia and myocardial infraction. And hypertension, hyperlipidemia, coronary artery disease, unstable angina, thrombosis, thrombin-induced platelet aggregation, and/or consequences occurring from thrombosis and/or the formation of atherosclerotic plaques.

Stroke and other ischemic brain diseases and/or neurodegeneration associated therewith, and the neurodegeneration of, or consequences of traumatic brain injury.

Sunburn, acne, vitiligo, alopecia arreata, photosensitivity disorders, albinism, canities (canities circumscripta), gray hair, dry skin and porphyria.

Neurodegenerative disorders such as depression, anxiety, compulsion (obsessive-compulsive disorder), neurosis, psychosis, insomnia/sleep disorder, sleep apnea, and drug or substance abuse.

Male sexual dysfunction such as impotence, loss of libido, and erectile dysfunction (including an inability to achieve or maintain an erection, ejaculatory failure, premature ejaculation, or inability to achieve an orgasm). Female sexual dysfunction such as sexual arousal disorder or disorders relating to desire, sexual receptivity, orgasm, and/or disturbances in trigger points of sexual function, and sexual pain, premature labor, dysmenorrhea, excessive menstruation, and endometriosis.

Bodyweight disorders such as obesity and anorexia (e.g., by altering appetite, metabolic rate, fat intake or carbohydrate craving); and diabetes mellitus (by enhancing glucose tolerance and/or decreasing insulin resistance).

Cancer of the lung, prostate, colon, breast, ovaries, and bone, skin (e.g., melanoma invasion), or angiogenic disorders including the formation or growth of solid tumors.

Fibrotic disorders such as hypertrophic scars, keloids, localized scleroderma, systematic sclerosis, sclerodermic graft versus host disease of the skin, cirrhosis of the liver, idiopathic and bleomycin induced lung fibrosis, and cyclosporin induced nephropathy.

Veterinary disease such as veterinary viral infections, including feline immunodeficiency virus, bovine immunodeficiency virus, and canine immunodeficiency virus.

Uveitis, especially in Behçet's syndrome and sarcoidosis, vasculitis and microbial infections.

The pharmaceutical and the cosmetic composition of this invention can be used in the form of pharmaceutical preparation, for example, in a solid, semisolid or liquid form, which contains the melanocortin receptor modulator, such as the compound of WS727713, as an active ingredient in admixture with an organic or inorganic carrier or excipient suitable for external, enteral or parenteral administrations. The active ingredient may be compounded, for example, with the usual non-toxic, pharmaceutically acceptable carriers for tablets, pellets, capsules, suppositories, solutions, emulsions, suspensions, injections, ointments, liniments, eye drops, lotion, gel, cream, and any other form suitable for use.

The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing reparations, in a solid, semisolid, or liquid form, and in addition auxiliary, stabilizing, thickening, solubilizing and coloring agents and perfumes may be used.

For applying the composition to human, it is preferable to apply it by intravenous, intramuscular, topical or oral administration. While the dosage of therapeutically effective amount of the melanocortin receptor modulator, such as the compound of WS727713, varies from and also depends upon the age and condition of each individual patient to be treated, when an individual patient is to be treated, in the case of intravenous administration, a daily dose of 0.001-100 mg of the melanocortin receptor modulator, such as the compound of WS727713, per kg weight of human being, in the case of intramuscular administration, a daily dose of 0.001-100 mg of the melanocortin receptor modulator, such as the compound of WS727713, per kg weight of human being, and in the case of oral administration, a daily dose of 0.01-320 mg of the melanocortin receptor modulator, such as the compound of WS727713, per kg weight of human being, is generally given for treatment.

Following examples are given for the purpose of illustrating the present invention in more detail.

EXAMPLE 1

(1) Fermentation of *Pseudonocardia* sp. No. 727713 for the production of WS727713:

A loopful of the slant culture was inoculated into 60 ml of sterilized seed culture medium containing 2% soluble starch, 0.8% yeast extract, and 0.5% agar (adjusted to pH 7.0 before sterilization) in a wide mouth 225 ml-Erlenmeyer flask. The flask was incubated at 30° C. for 7 days on a rotary shaker (220 rpm, 5.1 cm-throw) and then inoculated (2%) into 80 ml of the same sterilized medium in each of five wide mouth 225 ml-Erlenmeyer flasks. And the flasks were incubated at 30° C. for 4 days on a rotary shaker (220 rpm, 5.1 cm-throw).

The resultant seed culture was inoculated (2%) into 20 liters of sterilized production medium in 30-liter jar fermentor. The production medium was composed of 1% glucose, 1.5% soluble starch, 0.5% yeast extract, 1% β-cyclodextrin, 1% $CaCO_3$, 0.05% Adekanol LG-109 (Asahi Denka Kogyo K.K., Japan), and 0.05% Silicone KM-70 (Shin-Etsu Chemical Co., Ltd., Japan), the pH being adjusted to pH 7.0 before sterilization. The fermentation was carried out at 28° C. for 5 days under aeration of 20 liters/minute and agitation of 200 rpm.

The production of the WS727713 in the fermentation broth was monitored by HPLC analysis indicated below.

(Analytical HPLC Conditions)

| | |
|---|---|
| column | Mightysil RP-18 GP 150-4.6, 5 μm (5 μm, 4.6 mm ID × 150 mm L, Kanto Chemical Co., Ltd., Japan) |
| eluent | $CH_3CN:H_2O$ = 35:65 |
| flow rate | 1 ml/min. |
| temperature | room temperature |
| detection | UV at 210 nm |
| retention time | 9.3 min. |

(2) Isolation of WS727713:

After the culture was completed, the culture broth (16 liters) was extracted with an equal volume of acetone by stirring for a few minutes at room temperature. The extract was filtered with an aid of diatomaceous earth. The filtrate was concentrated in vacuo to give an aqueous solution (15 liters). The solution was applied to Diaion HP20 (Mitsubishi Chemical Co., Ltd.) column (800 ml), and the column washed with 20% acetonitrile (4 liters). The column was eluted with 40% acetonitrile (2.4 liters) and 60% acetonitrile (3.6 liters). The elute (6.0 liters) was diluted with water to 12 liters and passed through a column (1 liter) of Daisogel SP-120-ODS-B (15/30 μm, DAISO Co., Ltd., Japan) packed with water. The column was eluted with 32.5% acetonitrile. The elution was monitored by analytical HPLC indicated above. Fractions containing WS727713 were combined and concentrated in vacuo to give a powder. This powder was dissolved in a small amount of methanol and crystallized from water. The crystals were filtered and dried up to give 1.5 g of WS727713 as white needle.

INDUSTRIAL APPLICABILITY

The novel compound of the present invention has a melanocortin receptor modulatory activity, and is useful as an active ingredient of an anti-inflammatory agent and useful as a therapeutical or prophylactic agent for diseases responsive to regulation of melanocortin receptors.

This application is based on patent application No. 2004901919 filed in Australia, the contents of which are hereby incorporated by reference.

The invention claimed is:

1. A substantially pure WS727713 compound having the following properties:

a) Molecular formula: $C_{30}H_{44}N_8O_8$;

b) $^1$H Nuclear magnetic resonance spectrum:

(500 MHz, DMSO-d6) δ 9.76 (1H, s, exchangeable), 8.76 (1H, d, J=7.5 Hz, exchangeable), 8.23 (1H, d, J5 Hz, exchangeable), 7.76 (1H, dd, J=8.5 and 3 Hz, exchangeable), 7.25-7.17 (5H, m), 5.71 (1H, dd, J=10.5 and 5 Hz), 5.08 (1H, dd, J=11 and 4 Hz, exchangeable), 5.03 (1H, m), 4.99 (1H, m), 4.92 (1H, m), 4.85 (1H, m), 4.83 (1H, d, J=3 Hz, exchangeable), 4.76 (1H, br d, J=12 Hz, exchangeable), 4.12 (1H, dd, J=16.5 and 8.5 Hz), 3.65 (1H, dd, J=16.5 and 3 Hz), 3.58 (1H, m), 3.07 (1H, dd, J=13.5 and 8.5 Hz), 2.94 (1H, br d, J=13 Hz), 2.86 (1H, dd, J=13.5 and 6 Hz), 2.73-2.68 (2H, m), 2.58 (1H, m), 2.24 (1H, br d, J13 Hz), 2.08 (1H, br d, J=14 Hz), 1.88 (1H, m), 1.67 (1H, m), 1.55 (1H, m), 1.42-1.36 (2H, m), 1.21 (1H, m), 1.19 (3H, d, J=7 Hz), 1.09 (1H, m), 0.76 (3H, d, J=6.5 Hz), 0.75 (3H, d, J=6.5 Hz);

c) $^{13}$C Nuclear magnetic resonance spectrum:

(125 MHz, DMSO-d6) δ 173.8 (s), 171.7 (s), 170.4 (s), 169.8 (s), 169.1 (s), 167.6 (s), 137.2 (s), 129.2 (d)x2, 128.0 (d) x2, 126.3 (d), 60.2 (d), 53.2 (t), 51.1 (d), 50.8 (d), 49.6 (d), 47.4 (d), 47.0 (t), 44.7 (d), 41.2 (t), 36.4 (t), 35.4 (t), 33.2 (t), 23.6 (d), 23.5 (t), 23.1 (q), 21.7 (q), 21.0 (t), 15.8 (q).

2. A pharmaceutical composition containing the WS727713 compound of claim 1 or a salt thereof and a pharmaceutically acceptable, substantially non-toxic carrier or excipient.

3. A process for producing the WS727713 compound of claim 1, comprising culturing an *actinomycetes* strain of the genus *Pseudonocardia*, deposit number FERM BP-7570, in a culture medium under conditions suitable to produce compound WS727713 in a culture broth and recovering compound WS727713 from the culture broth.

* * * * *

UNITED STATES PATENT AND TRADEMARK OFFICE
CERTIFICATE OF CORRECTION

PATENT NO. : 7,741,085 B2  Page 1 of 1
APPLICATION NO. : 11/547729
DATED : June 22, 2010
INVENTOR(S) : Takanao Otsuka et al.

It is certified that error appears in the above-identified patent and that said Letters Patent is hereby corrected as shown below:

Claim 1, column 15, line 7, "J5 Hz" should read -- J=5 Hz --;

Claim 1, column 15, line 17, "J13 Hz" should read -- J=13 Hz --.

Signed and Sealed this

Fifth Day of October, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,741,085 B2 | Page 1 of 1 |
| APPLICATION NO. | : 11/547729 | |
| DATED | : June 22, 2010 | |
| INVENTOR(S) | : Otsuka et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 735 days.

Signed and Sealed this
Fifteenth Day of February, 2011

David J. Kappos
*Director of the United States Patent and Trademark Office*